United States Patent [19]

Kawasaki et al.

[11] Patent Number: 4,897,491

[45] Date of Patent: Jan. 30, 1990

[54] PROCESS FOR PRODUCING A GUANIDINE DERIVATIVE

[75] Inventors: Noboru Kawasaki; Yoshiaki Noguchi, both of Yokohama; Kenichi Fujii, Hiratsuka, all of Japan

[73] Assignee: Mitsui Toatsu Chemicals, Inc., Tokyo, Japan

[21] Appl. No.: 321,111

[22] Filed: Mar. 9, 1989

[30] Foreign Application Priority Data

Mar. 17, 1988 [JP] Japan .................................. 63-62008

[51] Int. Cl.$^4$ ........................................... C07D 233/64
[52] U.S. Cl. .................................................... 548/342
[58] Field of Search ........................................ 548/342

[56] References Cited

U.S. PATENT DOCUMENTS 3,755,363  8/1973  Timmons et al. ....................... 549/89
3,950,353  4/1976  Durant et al. ......................... 548/342
4,220,654  9/1980  Bolhofer et al. ................ 548/342 X

FOREIGN PATENT DOCUMENTS 0224612  6/1987  European Pat. Off. .
2445322  7/1980  France .

OTHER PUBLICATIONS

A. Omura, et al., *Bull. Chem. Soc. Japan*, 50(4), 914–916 (1977).

Primary Examiner—Richard A. Schwartz
Attorney, Agent, or Firm—Browdy and Neimark

[57] ABSTRACT

The guanidine derivative represented by the formula [III],

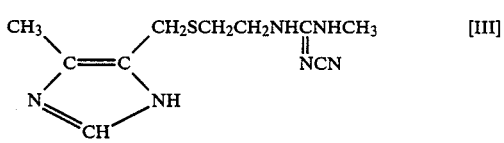

(commonly known under the name "Cimetidine") is produced by reaction of the compound represented by the formula [I],

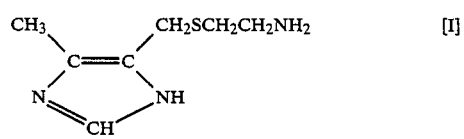

with a compound represented by the formula [II],

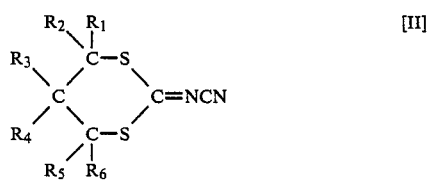

wherein $R_1$, $R_2$, $R_3$, $R_4$, $R_5$ and $R_6$, is each hydrogen atom, a lower alkyl group, phenyl group, or a radical of —$OR_7$ or —$COOR_7$, in which $R_7$ is hydrogen atom, a lower alkyl group or an alkali metal, followed by reaction with methylamine.

6 Claims, No Drawings

4,897,491

PROCESS FOR PRODUCING A GUANIDINE DERIVATIVE

FIELD OF THE INVENTION

This invention relates to a process for producing a guanidine derivative, N-cyano-N'-methyl-N''-[2-((4-methyl-5-imidazolyl)methylthio)ethyl]guanidine, represented by the formula [III], $$\begin{array}{c} CH_3 \\ \diagdown \\ N \\ \diagup \\ CH \end{array} C=C \begin{array}{c} CH_2SCH_2CH_2NHCNHCH_3 \\ \| \\ NCN \\ \diagup \\ NH \end{array} \quad [III]$$

The above compound [III] shows antagonistic action upon the $H_2$ receptor for histamine and is a useful drug for the treatment of gastric and duodenal ulcers (commonly known under the name of "Cimetidine").

BACKGROUND OF THE INVENTION

Prior Art

Various methods are known for producing the compound represented by the formula [III]. These include the method starting from 4-methyl-5-chloromethylimidazole (Japanese Patent Laid-Open No. 142271/1981), the method starting from 4-methyl-5-mercaptomethylimidazole (Japanese Patent Publication No. 40547/1979, No. 56709/1985, No. 40667/1986), and the method starting from a halogenated diacetyl. Also disclosed are the methods using, as starting material, the compound represented by the formula [I], $$\begin{array}{c} CH_3 \\ \diagdown \\ N \\ \diagup \\ CH \end{array} C=C \begin{array}{c} CH_2SCH_2CH_2NH_2 \\ \diagup \\ NH \end{array} \quad [I]$$

(Japanese Patent Publication No. 43832/1977, No. 1309/1981, No. 14460/1984).

Problems to be Solved by the Invention

Any of the conventional methods using, as starting material, the compound [I] uses a compound represented by the general formula [IV] as a second material, $$\begin{array}{c} CH_3S \\ \diagdown \\ CH_3X \end{array} C=NCN \quad [IV]$$

wherein X denotes O, S or NH. The reaction of compound [I] with compound [IV] generates a large volume of methyl mercaptan, $CH_3SH$, as a by-product, which is a highly toxic and flammable gas with very disagreeable odor. Hence, these methods involve safety and equipment problems when used as an industrial process.

Means to Solve the Problems

Intensive studies to solve the above-mentioned problems associated with the conventional methods have led us to find a new process for producing the compound [III] without using the compound [IV]. This invention was accomplished on the basis of this finding.

DETAILED DESCRIPTION OF THE INVENTION

This invention relates to a process for producing the guanidine derivative represented by the formula [III], $$\begin{array}{c} CH_3 \\ \diagdown \\ N \\ \diagup \\ CH \end{array} C=C \begin{array}{c} CH_2SCH_2CH_2NHCNHCH_3 \\ \| \\ NCN \\ \diagup \\ NH \end{array} \quad [III]$$

which comprises reacting the compound represented by the formula [I], $$\begin{array}{c} CH_3 \\ \diagdown \\ N \\ \diagup \\ CH \end{array} C=C \begin{array}{c} CH_2SCH_2CH_2NH_2 \\ \diagup \\ NH \end{array} \quad [I]$$

with a compound represented by the general formula [II], $$\begin{array}{c} R_2 \; R_1 \\ R_3 \diagdown \; | \\ \diagdown C-S \\ C \diagdown \\ R_4 \diagup \; C-S \\ \diagup \; | \\ R_5 \; R_6 \end{array} C=NCN \quad [II]$$

wherein $R_1$, $R_2$, $R_3$, $R_4$, $R_5$ and $R_6$, respectively, are hydrogen, lower alkyl, phenyl, or a radical of $-OR_7$ or $-COOR_7$, in which $R_7$ is hydrogen atom, a lower alkyl group or an alkali metal, followed by reaction with methylamine. Lower alkyl groups include alkyl groups having from about one to about three carbon atoms.

The compound [I] can be easily obtained, for example, by reaction of 4-methylimidazole with formaldehyde and cysteamine, and may be used in the process of this invention either in free form or as a salt (e.g., hydrochloride and sulfate).

The compound [II] can be easily obtained by reacting a compound represented by the general formula [V], $$\begin{array}{c} MS \\ \diagdown \\ \diagup \\ MS \end{array} C=NCN \quad [V]$$

wherein M denotes an alkali metal, with a compound represented by the general formula [VI], $$\begin{array}{c} R_2 \; R_3 \; R_5 \\ | \; | \; | \\ R_1-C-C-C-R_6 \\ | \; | \; | \\ X \; R_4 \; X \end{array} \quad [VI]$$

wherein $R_1$, $R_2$, $R_3$, $R_4$, $R_5$ and $R_6$ are as defined above, and X denotes a halogen atom.

The reaction between compound [I] and compound [II] is carried out under neutral or alkaline conditions. There is no need for pH control when the compound [I] is used in free form, while the reaction system must be maintained under neutral or alkaline conditions by addition of an alkali metal hydroxide or the like when the compound [I] is used as a salt.

The reaction product thus obtained may be isolated and purified before being subjected to the reaction with methylamine, or methylamine may be directly added to the reaction mixture obtained.

The reaction between compound [I] and compound [II] and the succeeding reaction with methylamine are both carried out in a solvent, such as alcohols (e.g., methanol and isopropanol) and acetonitrile, at a temperature in the range of 0° to 100° C., preferably in the range of 20° to 50° C., preferably in an inert gas atmosphere (e.g., nitrogen).

The first reaction is carried out at a molar ratio ([I]/[II]) of 0.9 to 1.1, and an excess amount of methylamine is used in the second reaction.

The compound [III] is separated from the by-products by commonly used techniques, such as solvent removal, extraction and filtration, and is then purified by recrystallization and other known techniques.

The process of this invention can thus produce the compound [III] very safely and at a low cost with no formation of by-product methyl mercaptan which is a toxic substance.

The following examples will further illustrate the invention.

EXAMPLE 1

4-Methyl-5-[(2-aminoethyl)thiomethyl]imidazole dihydrochloride 24.4 g (0.10 mole), N-cyano-2-imino-1,3-dithian 1 5.8 g (0.10 mole) and methanol 500 ml were mixed in a reaction flask, 160 g of 5% methanolic solution of sodium hydroxide was added dropwise to the resulting homogeneous solution through a dropping funnel at a temperature in the range of 25° to 30° C. over a period of two hours while slowly flowing nitrogen gas, and stirring was continued at that temperature for an additional two hours. After making sure that the 1,3-dithian compound had been consumed almost completely, 77 g (1.0 mole) of 40% methanolic solution of methylamine was added, and the reaction was continued at 20° to 25° C. for 24 hours.

The reaction mixture was concentrated, the concentrate was treated with chloroform to remove by-products, the residue was extracted with methanol, and the extract was concentrated to dryness. The solid thus obtained was recrystallized twice from isopropanol, giving 15.1 g of white crystals, which were identified as N-cyano-N'-methyl-N''-[2-((4-methyl-5-imidazolyl)methylthio)ethyl]guanidine by IR absorption analysis.

Melting point: 139°–140° C.

| Elemental analysis (wt %): as $C_{10}H_{16}N_6S$ | | | |
| --- | --- | --- | --- |
| Calcd. | C = 47.6 | H = 6.4 | N = 33.3 | S = 12.7 |
| Found | C = 47.3 | H = 6.3 | N = 33.4 | S = 12.8 |

EXAMPLE 2

N-cyano-2-imino-1,3-dithian 15.8 g (0.10 mole) and methanol 300 ml were placed in a reaction flask, methanolic solution of 4-methyl-5-[(2-aminoethyl)thiomethyl]imidazole 42.8 g (0.10 mole) was added dropwise with stirring at a temperature in the range of 20° to 25° C. over a period of two hours while slowly flowing nitrogen gas, and stirring was continued at that temperature for an additional two hours. After making sure that the 1,3-dithian compound had been consumed almost completely, 54 g (0.7 mole) of 40% methanolic solution of methylamine was added, and the reaction was continued at 20° to 25° C. for 24 hours. Analysis of the reaction mixture thus obtained by liquid chromatography showed the formation of N-cyano-N'-methyl-N''[2-((4-methyl-5-imidazolyl)methylthio)ethyl]guanidine with a yield of 80%.

Liquid chromatography
Liquid chromatograph: Shimazu LC-5A
Column: Unisil Q CN, 4.60×250 mm
Mobile phase: 0.01M-$(NH_4)H_2PO_4$ aq. soln.: $CH_3OH$:$CH_3CN$=15:15:70 (pH 3.5)
Flow rate: 1 ml/min
Detection: UV (229 nm)

EXAMPLE 3

4-Methyl-5-[(2-aminoethyl)thiomethyl]imidazole dihydrochloride 24.4 g (0.10 mole), N-cyano-2-imino-4-methyl-1,3-dithian 15.5 g (0.09 mole) and methanol 500 ml were placed in a reaction flask, 160 g of 5% methanolic solution of sodium hydroxide was added dropwise with stirring at a temperature in the range of 30° to 35° C. over a period of three hours while slowly flowing nitrogen gas, and stirring was continued at that temperature for an additional three hours. After making sure that the 1,3-dithian compound had been consumed almost completely, 78 g (1.0 mole) of 40% methanolic solution of methylamine was added, and the reaction was continued at 25° to 30° C. for 24 hours. Analysis of the reaction mixture thus obtained by liquid chromatography showed the formation of N-cyano-N'-methyl-N''[2-((4-methyl-5-imidazolyl)methylthio)ethyl]guanidine with a yield of 73%.

Effects Achieved by the Invention

It was found that compounds represented by the general formula [II] can be used as the starting material for the synthesis of N-cyano-N'-methyl-N''-[2-((4-methyl-5-imidazolyl)methylthio)ethyl]guanidine. Based on this finding, the present invention provides a new process for producing this guanidine derivative safely and at a low cost with no formation of by-product methyl mercaptan (a toxic and flammable gas with very disagreeable odor), which formation is unavoidable with conventional methods.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiment. It is to be understood that the phraseology or terminology herein is for the purpose of description and not of limitation.

What is claimed is:

1. A process for producing a guanidine derivative represented by the formula [III],

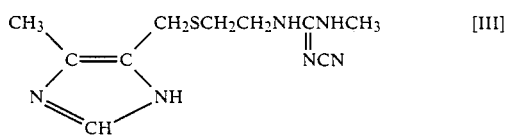

which comprises reacting a compound represented by the formula [I],

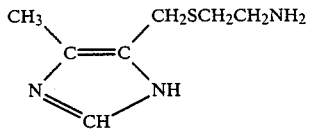 [I]

with a compound represented by the formula [II],

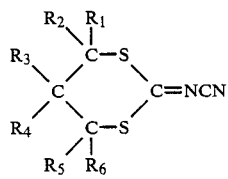 [II]

wherein $R_1$, $R_2$, $R_3$, $R_4$, $R_5$ and $R_6$, are selected from the group consisting of hydrogen, lower alkyl, phenyl, and a radical of the formula $-OR_7$ or $-COOR_7$, in which $R_7$ is selected from the group consisting of hydrogen, lower alkyl and alkali metal, followed by reaction with methylamine.

2. The process according to claim 1, in which in the compound represented by the formula [II], $R_1$, $R_2$, $R_3$, $R_4$, $R_5$ and $R_6$, respectively, are a hydrogen atom or a lower alkyl group.

3. The process according to claim 1, in which in the compound represented by the formula [II], $R_1$, $R_2$, $R_3$, $R_4$, $R_5$ and $R_6$, respectively, are all a hydrogen atom.

4. The process according to claim 1, in which the first and second reactions are carried out at a temperature in the range of 0° to 100° C.

5. The process according to claim 4 wherein said temperature range is 20° to 50° C.

6. The process according to claim 1, in which the first reaction is carried out at a molar ratio ([I]/[II]) of 0.9 to 1.1.

* * * * *